US012685965B1

(12) United States Patent
Yao

(10) Patent No.: US 12,685,965 B1
(45) Date of Patent: Jul. 21, 2026

(54) **USE OF *ASPERGILLUS CEJPII* IN METABOLISM OF FLAMMABLE AND EXPLOSIVE GAS**

(71) Applicants: Xi'an Polytechnic University, Xi'an (CN); Northwest A&F University Shenzhen Research Inst, Shenzhen (CN)

(72) Inventor: Yiqing Yao, Shenzhen (CN)

(73) Assignees: Xi'an Polytechnic University, Xi'an (CN); Northwest A&F University Shenzhen Research Inst, Shenzhen (CN)

( * ) Notice: Subject to any disclaimer, the term of this patent is extended or adjusted under 35 U.S.C. 154(b) by 0 days.

(21) Appl. No.: 19/353,922

(22) Filed: Oct. 9, 2025

(30) Foreign Application Priority Data

Aug. 19, 2025 (CN) .......................... 202511157019.1

(51) Int. Cl.
*B01D 53/84* (2006.01)
*C12N 1/145* (2026.01)
*C12R 1/66* (2006.01)

(52) U.S. Cl.
CPC ............. *B01D 53/84* (2013.01); *C12N 1/145* (2021.05); *B01D 2251/95* (2013.01); *B01D 2257/108* (2013.01); *B01D 2257/7025* (2013.01); *C12R 2001/66* (2021.05)

(58) Field of Classification Search
CPC ................ B01D 53/84; B01D 2251/95; B01D 2257/108; B01D 2257/7025; C12N 1/145; C12R 2001/66
See application file for complete search history.

(56) References Cited

PUBLICATIONS

Techaoei et al., Saudi Journal of Biological Sciences, vol. 27, Issue 11, 2020, pp. 2883-2889, doi.org/10.1016/j.sjbs.2020.08.037. (Year: 2020).*

* cited by examiner

*Primary Examiner* — Kade Ariani
(74) *Attorney, Agent, or Firm* — Edell, Shapiro & Finnan, LLC

(57) ABSTRACT

*Aspergillus cejpii* is used in metabolism of a flammable and explosive gas. It has been determined that *Aspergillus cejpii* S8 exhibits an excellent absorption and metabolism effect for a flammable and explosive gas such as hydrogen and methane, and a mixed gas including the flammable and explosive gas. The *Aspergillus cejpii* S8 strain can undergo a metabolic process with a flammable and explosive gas or a mixed gas including the flammable and explosive gas as a carbon source and/or an energy source, thereby achieving the efficient treatment of the flammable and explosive gas or the mixed gas including the same. The *Aspergillus cejpii* S8 strain demonstrates high environmental safety and a prominent removal effect and can be conveniently used without toxic and side effects, which facilitates the application and transformation.

5 Claims, No Drawings

USE OF *ASPERGILLUS CEJPII* IN METABOLISM OF FLAMMABLE AND EXPLOSIVE GAS

CROSS-REFERENCE TO RELATED APPLICATION

This patent application claims the benefit of and priority to Chinese Patent Application No. 202511157019.1 filed with the China National Intellectual Property Administration on Aug. 19, 2025, the disclosure of which is incorporated by reference herein in its entirety as part of the present application.

TECHNICAL FIELD

The present disclosure belongs to the technical field of microorganisms, and specifically relates to the use of *Aspergillus cejpii* in metabolism of a flammable and explosive gas.

BACKGROUND

Flammable and explosive gases refer to a class of gases that can be mixed with air to produce combustible mixtures with an explosive range of 20% to 80%. Common flammable and explosive gases include hydrogen ($H_2$), methane ($CH_4$), carbon monoxide (CO), etc. Flammable and explosive gases are prone to leakage and combustion, have relatively-low explosive limits, and are extremely hazardous. Flammable and explosive gases can trigger industrial accidents or fires, posing severe threats to the local ecosystems and the human safety. Therefore, it is necessary to distinguish and classify these gases during production, transportation, storage, and usage.

Studies have shown that microorganisms play a significant role in the catabolism of flammable and explosive gases, and can contribute to the regulation of ecosystems. Moreover, the catabolism of flammable and explosive gases with microorganisms can be easily implemented, and is free of toxic and side effects.

*Aspergillus* is a filamentous fungus widely distributed on grains and various organic matters and in the air and soil. *Aspergillus* is an important strain in the fermentation industry and food processing industry. Nearly 60 *Aspergillus* species have been utilized primarily for wine-making, vinegar production, etc. However, *Aspergillus* is rarely used in the metabolism of gases, especially in the metabolism of flammable and explosive gases.

SUMMARY

An objective of the present disclosure is to provide a use of *Aspergillus cejpii* in metabolism of a flammable and explosive gas. The *Aspergillus cejpii* S8 in the present disclosure exhibits an excellent absorption and metabolism effect for a flammable and explosive gas and a mixed gas including the flammable and explosive gas, which expands the biological use of *Aspergillus cejpii* S8.

The present disclosure provides a use of *Aspergillus cejpii* S8 in metabolism of a gas, where the gas includes hydrogen or a mixed gas including a flammable and explosive gas; the flammable and explosive gas includes hydrogen and/or methane; and an accession number of the *Aspergillus cejpii* S8 is CGMCC NO. 40828.

The present disclosure also provides a use of a microbial agent including *Aspergillus cejpii* S8 in metabolism of a gas, where the gas includes hydrogen or a mixed gas including a flammable and explosive gas; the flammable and explosive gas includes hydrogen and/or methane; and an accession number of the *Aspergillus cejpii* S8 is CGMCC NO. 40828.

Preferably, the microbial agent includes a suspension of *Aspergillus cejpii* S8.

Preferably, the mixed gas includes one or more mixed gases selected from the group consisting of the following four items:

1) hydrogen and carbon dioxide;
2) hydrogen and methane;
3) methane and carbon dioxide; and
4) hydrogen, methane, and carbon dioxide.

Preferably, in the mixed gas of 1), a volume ratio of hydrogen to carbon dioxide is (1-2):(1-2).

Preferably, in the mixed gas of 2), a volume ratio of hydrogen to methane is (1-2):(1-2).

Preferably, in the mixed gas of 3), a volume ratio of methane to carbon dioxide is (1-2):(1-2).

Preferably, in the mixed gas of 4), hydrogen, methane, and carbon dioxide are in a volume ratio of 1:1:1.

The present disclosure also provides a method for metabolizing a gas, including treating the gas with *Aspergillus cejpii* S8 or a microbial agent including the strain of *Aspergillus cejpii* S8, where the gas is hydrogen or a mixed gas including a flammable and explosive gas; the flammable and explosive gas includes hydrogen and/or methane; and an accession number of the strain of *Aspergillus cejpii* S8 is CGMCC NO. 40828.

Preferably, the microbial agent is a suspension of the strain of *Aspergillus cejpii* S8.

Beneficial Effects:

The present disclosure provides a use of *Aspergillus cejpii* S8 in metabolism of a gas. The gas includes hydrogen or a mixed gas including a flammable and explosive gas. The flammable and explosive gas includes hydrogen and/or methane. The accession number of *Aspergillus cejpii* S8 is CGMCC NO. 40828. It is found in the present disclosure that *Aspergillus cejpii* S8 exhibits an excellent absorption and metabolism effect for a flammable and explosive gas such as hydrogen and methane, and a mixed gas including the flammable and explosive gas. The *Aspergillus cejpii* S8 strain can undergo a metabolic process with a flammable and explosive gas or a mixed gas including the flammable and explosive gas as a carbon source and/or an energy source, thereby achieving the efficient treatment of the flammable and explosive gas or the mixed gas including the same. The *Aspergillus cejpii* S8 strain demonstrates high environmental safety and a prominent removal effect, and can be conveniently used without toxic and side effects, which facilitates the application and transformation.

Biological Deposit Statement

*Aspergillus cejpii* was deposited in the China General Microbiological Culture Collection Center (CGMCC) on Sep. 20, 2023, with the deposit number CGMCC No. 40828, and the deposit address is No. 3, Yard 1, Beichen West Road, Chaoyang District, Beijing, China.

DETAILED DESCRIPTION

The present disclosure provides a use of *Aspergillus cejpii* S8 in metabolism of a gas. The gas includes hydrogen or a mixed gas including a flammable and explosive gas. The flammable and explosive gas includes hydrogen and/or methane. The accession number of the strain of *Aspergillus*

*cejpii* S8 is CGMCC NO. 40828. The strain of *Aspergillus cejpii* S8 in the present disclosure has been disclosed in the patent CN202311542973.3.

The present disclosure also provides a use of a microbial agent including *Aspergillus cejpii* S8 in metabolism of a gas. The gas includes hydrogen or a mixed gas including a flammable and explosive gas. The flammable and explosive gas includes hydrogen and/or methane. The accession number of the strain of *Aspergillus cejpii* S8 is CGMCC NO. 40828.

As an embodiment, the microbial agent is a suspension of *Aspergillus cejpii* S8. As another embodiment, an effective viable cell concentration in the suspension of *Aspergillus cejpii* S8 is 2% (vol/vol). As an embodiment, a resuspension agent for the suspension of *Aspergillus cejpii* S8 is phosphate buffered saline (PBS). The PBS is 1×PBS with a pH of 6.8.

As an embodiment, a preparation method of the suspension of *Aspergillus cejpii* S8 is as follows: The *Aspergillus cejpii* S8 is inoculated into an inorganic salt medium and cultured under shaking to produce an *Aspergillus cejpii* S8 fermentation broth. The *Aspergillus cejpii* S8 fermentation broth is subjected to solid-liquid separation to produce a precipitate. The precipitate is resuspended to produce the suspension of *Aspergillus cejpii* S8. As an embodiment, the inorganic salt medium includes 0.5 g/L of $KH_2PO_4$, 0.5 g/L of $Na_2HPO_4$, 0.4 g/L of NaCl, 1.0 g/L of $KNO_3$, 0.5 g/L of $NH_4Cl$, 1.0 g/L of $MgSO_4·7H_2O$, 0.2 g/L of $CaCl_2$, 0.004 g/L of $FeSO_4·7H_2O$, 0.004 g/L of $CuSO_4·5H_2O$, 0.004 g/L of $MnSO_4·H_2O$, 0.004 g/L of $ZnSO_4·7H_2O$, and 0.00024 g/L of $NaMoO_4·2H_2O$. As an embodiment, the culturing under shaking is conducted at 28° C. As an embodiment, the culturing under shaking is conducted at a rotational speed of 170 rpm. As an embodiment, the culturing under shaking is conducted for 3 days.

As an embodiment, the mixed gas includes one or more mixed gases selected from the group consisting of the following four items: 1) hydrogen and carbon dioxide; 2) hydrogen and methane; 3) methane and carbon dioxide; and 4) hydrogen, methane, and carbon dioxide.

As an embodiment, in the mixed gas of 1), a volume ratio of hydrogen to carbon dioxide is (1-2):(1-2). As another embodiment, the volume ratio of hydrogen to carbon dioxide is 1:1, 1:2, or 2:1. As an embodiment, in the mixed gas of 2), a volume ratio of hydrogen to methane is (1-2):(1-2). As another embodiment, the volume ratio of hydrogen to methane is 1:1, 1:2, or 2:1. As an embodiment, in the mixed gas of 3), a volume ratio of methane to carbon dioxide is (1-2):(1-2). As another embodiment, the volume ratio of methane to carbon dioxide is 1:1, 1:2, or 2:1. As an embodiment, in the mixed gas of 4), hydrogen, methane, and carbon dioxide are in a volume ratio of 1:1:1.

The present disclosure also provides a method for metabolizing a gas, including: treating the gas with *Aspergillus cejpii* S8 or a microbial agent including *Aspergillus cejpii* S8. The gas is hydrogen or a mixed gas including a flammable and explosive gas. The flammable and explosive gas includes hydrogen and/or methane. The accession number of *Aspergillus cejpii* S8 is CGMCC NO. 40828.

As an embodiment, the microbial agent is a suspension of *Aspergillus cejpii* S8. The relevant characteristics of the suspension of *Aspergillus cejpii* S8 have been defined in the aforementioned technical solution, and will not be repeated here. As an embodiment, a volume of the suspension of *Aspergillus cejpii* S8 is 2% of the volume of the gas.

In order to further illustrate the present disclosure, the technical solutions provided by the present disclosure are described in detail below in connection with examples, but these examples should not be construed as limiting the claimed scope of the present disclosure.

The experimental methods and detection methods in the following examples are conventional methods, unless otherwise specified. The reagents and materials in the following examples can be obtained through conventional commercial channels, unless otherwise specified.

Inorganic salt medium: 0.5 g/L of $KH_2PO_4$, 0.5 g/L of $Na_2HPO_4$, 0.4 g/L of NaCl, 1.0 g/L of $KNO_3$, 0.5 g/L of $NH_4Cl$, 1.0 g/L of $MgSO_4·7H_2O$, 0.2 g/L of $CaCl_2$, 0.004 g/L of $FeSO_4·7H_2O$, 0.004 g/L of $CuSO_4·5H_2O$, 0.004 g/L of $MnSO_4·H_2O$, 0.004 g/L of $ZnSO_4·7H_2O$, and 0.00024 g/L of $NaMoO_4·2H_2O$.

Potato dextrose agar (PDA) medium: 200 g/L of potato, 20 g/L of glucose, 5 g/L of peptone, 3 g/L of monopotassium phosphate, 1.5 g/L of magnesium sulfate, and 20 g/L of agar.

Example 1

In this example, the effect of *Aspergillus cejpii* S8 on utilization of a $H_2$ gas was tested, including the following steps:

50 mL of inorganic salt medium was added to a 250 mL sealed bottle, a headspace gas in the sealed bottle was replaced with nitrogen, and a pure gas of $H_2$ was introduced into the sealed bottle. An *Aspergillus cejpii* S8 suspension isolated and purified was inoculated into each bottle at an inoculum size of 2%. Ambient air was introduced into a control bottle to establish a control group. Static culture was conducted at a constant temperature of 28° C. for 7 days. Then, the following indexes were determined:

The utilization rate of $H_2$ by *Aspergillus cejpii* S8 was determined using gas chromatography-mass spectrometry (GC2014C, purchased from Shimadzu) under the following test conditions: TCD detector; inlet temperature: 100° C.; detector temperature: 100° C.; oven temperature: 90° C.; carrier gas: argon; and flow rate: 30 mL/min. Determination results are shown in Table 1.

The average volumetric utilization rate was determined by a drainage method. Determination results are shown in Table 1.

The dry mycelium weight was determined as follows: a filter paper was first oven-dried to a constant weight, and accurately weighed. An *Aspergillus cejpii* S8 fermentation broth was thoroughly mixed, and then 30 mL of the *Aspergillus cejpii* S8 fermentation broth was accurately taken and subjected to vacuum filtration to produce a filter residue. The filter residue was washed multiple times with distilled water until the resulting washing solution was colorless, and then oven-dried in a constant-temperature drying oven at 55° C. to a constant weight. The total mass of the dried filter residue and filter paper was accurately measured. The dry mycelium weight was calculated according to the following formula: dry mycelium weight (mg)=total mass of the dried filter residue and filter paper (mg)−mass of the dried filter paper (mg). Determination results are shown in Table 1.

TABLE 1

| Utilization efficiency of $H_2$ gas by *Aspergillus cejpii* S8 | | | |
|---|---|---|---|
| Index | Gas utilization rate (%) | Volumetric utilization rate (%) | Dry mycelium weight (mg) |
| Control group | 2.016 | 2.437 | 24.178 |
| Treatment group | 95.721 | 51.110 | 41.833 |
| Utilization ratio | 47.480 times | 20.972 times | 1.730 times |

As shown in Table 1, after *Aspergillus cejpii* S8 was added to a sealed bottle with ambient air, the gas utilization rate for the ambient air was only 2.016%, the volumetric utilization rate for the ambient air was 2.437%, and the dry mycelium weight was 28.178 mg. After *Aspergillus cejpii* S8 was added to the pure $H_2$ gas, the $H_2$ gas could be significantly utilized. This strain could efficiently utilize the $H_2$ gas as a nutrient for growth and reproduction. This strain demonstrated a utilization rate of 95.721% and a volumetric utilization rate of 51.110% for the $H_2$ gas and corresponded to a dry mycelium weight of 41.833 mg. *Aspergillus cejpii* S8 enabled the gas utilization rate of the pure $H_2$ gas to be 47.480 times higher than the gas utilization rate of the control group, the volumetric utilization rate of the pure $H_2$ gas to be 20.972 times higher than the volumetric utilization rate of the control group, and the dry mycelium weight to be 1.730 times higher than the dry mycelium weight of the control group. It can be known that the *Aspergillus cejpii* S8 strain provided by the present disclosure demonstrates a prominent utilization effect for the $H_2$ gas with a strong $H_2$ utilization capacity and can utilize the $H_2$ gas as a nutrient for growth and reproduction.

Example 2

In this example, the effect of *Aspergillus cejpii* S8 on utilization a mixed gas of $CO_2$ and $H_2$ was tested, including the following steps:

50 mL of inorganic salt medium was added to a 250 mL sealed bottle, a headspace gas in the sealed bottle was replaced with nitrogen, and the mixed gas of $CO_2$ and $H_2$ was introduced into the sealed bottle. The following three groups were set according to volume ratios: CH1 ($CO_2$: $H_2$=1:2), CH2 ($CO_2$:$H_2$=1:1), and CH3 ($CO_2$:$H_2$=2:1). A mixed gas with a specified volume ratio was replenished into corresponding sealed bottles every 7 days. The 7 days was defined as one cycle. The replenishing was repeated four times. An *Aspergillus cejpii* S8 suspension isolated and purified was inoculated into each bottle at an inoculum size of 2%. Ambient air was introduced into a control bottle to establish a control group.

Static culture was conducted at a constant temperature of 28° C. for 7 days. The average utilization rate of the mixed gas of $CO_2$ and $H_2$ by *Aspergillus cejpii* S8 in 4 cycles was determined using gas chromatography-mass spectrometry (GC2014C, purchased from Shimadzu) (that is, the utilization rate in each cycle was determined and then an average was taken, which was the same for the following examples). Determination results are shown in Table 2. Test conditions were the same as in Example 1. The average volumetric utilization rate in 4 cycles was determined by a drainage method (that is, the volumetric utilization rate in each cycle was determined and then an average was taken, which was the same for the following examples). Determination results are shown in Table 2. The dry mycelium weight in the fourth cycle was determined by the same method as in Example 1. Determination results are shown in Table 2.

TABLE 2

| Utilization efficiency of $CO_2/H_2$ mixed gas by *Aspergillus cejpii* S8 in 4 cycles | | | |
|---|---|---|---|
| Index | Gas utilization rate (%) | Volumetric utilization rate (%) | Dry mycelium weight (mg) |
| Control group | 3.124 | 3.560 | 30.561 |
| CH1 group | 95.043 | 60.206 | 43.8 |
| Utilization ratio | 30.423 times | 16.911 times | 1.433 times |
| CH2 group | 95.507 | 63.663 | 46.13 |
| Utilization ratio | 30.572 times | 17.882 times | 1.509 times |
| CH3 group | 96.524 | 63.404 | 48.03 |
| Utilization ratio | 30.897 times | 17.810 times | 1.571 times |

As shown in Table 2, after *Aspergillus cejpii* S8 was added to a sealed bottle with ambient air, the gas utilization rate for the ambient air was only 3.124%, the volumetric utilization rate for the ambient air was 3.560%, and the dry mycelium weight was 30.561 mg. After *Aspergillus cejpii* S8 was added to the $CO_2/H_2$ mixed gas, the CH3 group exhibited the most significant utilization capacity, followed by the CH2 group and then the CH1 group. This strain could efficiently utilize the $CO_2/H_2$ mixed gas as both a carbon source and an energy source for growth and reproduction. The CH3 group demonstrated a utilization rate of 96.524% and a volumetric utilization rate of 63.404% for the $CO_2/H_2$ mixed gas and corresponded to a dry mycelium weight of 48.03 mg. In the CH3 group, *Aspergillus cejpii* S8 enabled the gas utilization rate of the $CO_2/H_2$ mixed gas to be 30.897 times higher than the gas utilization rate of the control group, the volumetric utilization rate of the $CO_2/H_2$ mixed gas to be 17.810 times higher than the volumetric utilization rate of the control group, and the dry mycelium weight to be 1.571 times higher than the dry mycelium weight of the control group. It can be known that the *Aspergillus cejpii* S8 strain provided by the present disclosure demonstrates a prominent utilization effect for the $CO_2/H_2$ mixed gas with a strong $CO_2/H_2$ utilization capacity and can utilize the $CO_2/H_2$ mixed gas as a carbon source and an energy source for growth and reproduction.

Example 3

In this example, the effect of *Aspergillus cejpii* S8 on utilization a mixed gas of $CH_4$ and $H_2$ was tested, including the following steps:

50 mL of inorganic salt medium was added to a 250 mL sealed bottle, a headspace gas in the sealed bottle was replaced with nitrogen, and the mixed gas of $CH_4$ and $H_2$ was introduced into the sealed bottle. The following three groups were set according to volume ratios: MH1 ($CH_4$: $H_2$=1:2), MH2 ($CH_4$:$H_2$=1:1), and MH3 ($CH_4$:$H_2$=2:1). A mixed gas with a specified volume ratio was replenished into corresponding sealed bottles every 7 days. The 7 days was defined as one cycle. The replenishing was repeated four times. An *Aspergillus cejpii* S8 suspension isolated and purified was inoculated into each bottle at an inoculum size of 2%. Ambient air was introduced into a control bottle to establish a control group.

Static culture was conducted at a constant temperature of 28° C. for 7 days. The average utilization rate of the mixed gas of $CH_4$ and $H_2$ by *Aspergillus cejpii* S8 in 4 cycles was determined using gas chromatography-mass spectrometry (GC2014C, purchased from Shimadzu). Determination results are shown in Table 3. Test conditions were the same as in Example 1. The average volumetric utilization rate in 4 cycles was determined by a drainage method. Determination results are shown in Table 3. A dry mycelium weight in the fourth cycle was determined by the same method as in Example 2. Determination results are shown in Table 3.

TABLE 3

Utilization efficiency of $CH_4/H_2$ mixed gas by
*Aspergillus cejpii* S8 in 4 cycles

| Index | Gas utilization rate (%) | Volumetric utilization rate (%) | Dry mycelium weight (mg) |
|---|---|---|---|
| Control group | 3.124 | 3.560 | 30.561 |
| MH1 group | 91.500 | 48.743 | 86.432 |
| Utilization ratio | 29.289 times | 13.691 times | 2.828 times |
| MH2 group | 93.428 | 51.942 | 89.234 |
| Utilization ratio | 29.906 times | 14.590 times | 2.919 times |
| MH3 group | 94.620 | 54.958 | 89.350 |
| Utilization ratio | 30.288 times | 15.437 times | 2.923 times |

As shown in Table 3, after *Aspergillus cejpii* S8 was added to a sealed bottle with ambient air, the gas utilization rate for the ambient air was only 3.124%, the volumetric utilization rate for the ambient air was 3.560%, and the dry mycelium weight was 30.561 mg. After *Aspergillus cejpii* S8 was added to a $CH_4/H_2$ mixed gas, the MH3 group exhibited the most significant utilization capacity, followed by the MH2 group and then the MH1 group. This strain could efficiently utilize the $CH_4/H_2$ mixed gas as both a carbon source and an energy source for growth and reproduction. The MH3 group demonstrated a utilization rate of 94.620% and a volumetric utilization rate of 54.958% for the $CH_4/H_2$ mixed gas, and corresponded to the dry mycelium weight of 89.350 mg. In the MH3 group, *Aspergillus cejpii* S8 enabled the gas utilization rate of the $CH_4/H_2$ mixed gas to be 30.288 times higher than the gas utilization rate of the control group, the volumetric utilization rate of the $CH_4/H_2$ mixed gas to be 15.437 times higher than the volumetric utilization rate of the control group, and the dry mycelium weight to be 2.923 times higher than the dry mycelium weight of the control group. It can be known that the *Aspergillus cejpii* S8 strain provided by the present disclosure demonstrates a prominent utilization effect for the $CH_4/H_2$ mixed gas with a strong $CH_4/H_2$ utilization capacity and can utilize the $CH_4/H_2$ mixed gas as a carbon source and an energy source for growth and reproduction.

Example 4

In this example, the effect of *Aspergillus cejpii* S8 utilization of a mixed gas of $CO_2$ and $CH_4$ was tested, including the following steps:

50 mL of inorganic salt medium was added to a 250 mL sealed bottle, a headspace gas in the sealed bottle was replaced with nitrogen, and the mixed gas of $CO_2$ and $CH_4$ was introduced into the sealed bottle. The following three groups were set according to volume ratios: CM1 ($CO_2$: $CH_4$=1:2), CM2 ($CO_2$:$CH_4$=1:1), and CM3 ($CO_2$:$CH_4$=2:1). A mixed gas with a specified volume ratio was replenished into corresponding sealed bottles every 7 days. The 7 days was defined as one cycle. The replenishing was repeated four times. An *Aspergillus cejpii* S8 suspension isolated and purified was inoculated into each bottle at an inoculum size of 2%. Ambient air was introduced into a control bottle to establish a control group.

8

Static culture was conducted at a constant temperature of 28° C. for 7 days. The average utilization rate of the mixed gas of $CO_2$ and $CH_4$ by *Aspergillus cejpii* S8 in 4 cycles was determined using gas chromatography-mass spectrometry (GC2014C, purchased from Shimadzu). Determination results are shown in Table 4. Test conditions were the same as in Example 1. The average volumetric utilization rate in 4 cycles was determined by a drainage method. Determination results are shown in Table 4. The dry mycelium weight in the fourth cycle was determined by the same method as in Example 1. Determination results are shown in Table 4.

TABLE 4

Utilization efficiency of $CO_2/CH_4$ mixed gas by
*Aspergillus cejpii* S8 in 4 cycles

| Index | Gas utilization rate (%) | Volumetric utilization rate (%) | Dry mycelium weight (mg) |
|---|---|---|---|
| Control group | 3.124 | 3.560 | 30.561 |
| CM1 group | 94.361 | 65.966 | 90.567 |
| Utilization ratio | 30.205 times | 18.529 times | 2.963 times |
| CM2 group | 95.877 | 69.896 | 91.867 |
| Utilization ratio | 30.690 times | 19.633 times | 3.006 times |
| CM3 group | 97.014 | 73.632 | 91.771 |
| Utilization ratio | 31.054 times | 20.683 times | 3.002 times |

As shown in Table 4, after *Aspergillus cejpii* S8 was added to a sealed bottle with ambient air, the gas utilization rate for the ambient air was only 3.124%, the volumetric utilization rate for the ambient air was 3.560%, and the dry mycelium weight was 30.561 mg. After *Aspergillus cejpii* S8 was added to the $CO_2/CH_4$ mixed gas, the CM3 group exhibited the most significant utilization capacity, followed by the CM2 group and then the CM1 group. This strain could efficiently utilize the $CO_2/CH_4$ mixed gas as both a carbon source and an energy source for growth and reproduction. The CM3 group demonstrated a utilization rate of 97.014% and a volumetric utilization rate of 73.632% for the $CO_2/CH_4$ mixed gas and corresponded to a dry mycelium weight of 91.771 mg. In the CM3 group, *Aspergillus cejpii* S8 enabled the gas utilization rate of the $CO_2/CH_4$ mixed gas to be 31.054 times higher than the gas utilization rate of the control group, the volumetric utilization rate of the $CO_2/$ $CH_4$ mixed gas to be 20.683 times higher than the volumetric utilization rate of the control group, and the dry mycelium weight to be 3.002 times higher than the dry mycelium weight of the control group. It can be known that the *Aspergillus cejpii* S8 strain provided by the present disclosure demonstrates a prominent utilization effect for the $CO_2/CH_4$ mixed gas with a strong $CO_2/CH_4$ utilization capacity and can utilize the $CO_2/CH_4$ mixed gas as a carbon source and an energy source for growth and reproduction.

Example 5

In this example, the effect of *Aspergillus cejpii* S8 on utilization of a mixed gas of $CO_2$, $CH_4$, and $H_2$ was tested, including the following steps:

50 mL of inorganic salt medium was added to a 250 mL sealed bottle, a headspace gas in the sealed bottle was replaced with nitrogen, and the mixed gas of $CO_2$, $CH_4$, and $H_2$ in a volume ratio of 1:1:1 was introduced into the sealed bottle. A mixed gas with a specified volume ratio was replenished into corresponding sealed bottles every 7 days. The 7 days was defined as one cycle. The replenishing was repeated four times. An *Aspergillus cejpii* S8 suspension isolated and purified was inoculated into each bottle at an inoculum size of 2%. Ambient air was introduced into a control bottle to establish a control group.

Static culture was conducted at a constant temperature of 28° C. for 7 days. The average utilization rate of the mixed gas of $CO_2$, $CH_4$, and $H_2$ by *Aspergillus cejpii* S8 in 4 cycles was determined using gas chromatography-mass spectrometry (GC2014C, purchased from Shimadzu). Determination results are shown in Table 5. Test conditions were the same as in Example 1. The average volumetric utilization rate in 4 cycles was determined by a drainage method. Determination results are shown in Table 5. The dry mycelium weight in the fourth cycle was determined by the same method as in Example 1. Determination results are shown in Table 5.

TABLE 5

Utilization efficiency of $CO_2$/$CH_4$/$H_2$ mixed gas by
*Aspergillus cejpii* S8 in 4 cycles

| Index | Gas utilization rate (%) | Volumetric utilization rate (%) | Dry mycelium weight (mg) |
|---|---|---|---|
| Control group | 3.124 | 3.560 | 30.561 |
| Treatment group | 94.722 | 59.196 | 86.768 |
| Utilization ratio | 30.321 times | 16.628 times | 2.839 times |

As shown in Table 5, after *Aspergillus cejpii* S8 was added to a sealed bottle with ambient air, the gas utilization rate for the ambient air was only 3.124%, the volumetric utilization rate for the ambient air was 3.560%, and the dry mycelium weight was 30.561 mg. After *Aspergillus cejpii* S8 was added to the $CO_2$/$CH_4$/$H_2$ mixed gas, the treatment group exhibited a significant utilization capacity. This strain could efficiently utilize the $CO_2$/$CH_4$/$H_2$ mixed gas as both a carbon source and an energy source for growth and reproduction. The treatment group demonstrated a utilization rate of 94.722% and a volumetric utilization rate of 59.196% for the $CO_2$/$CH_4$/$H_2$ mixed gas and corresponded to a dry mycelium weight of 86.768 mg. *Aspergillus cejpii* S8 enabled the gas utilization rate of the $CO_2$/$CH_4$/$H_2$ mixed gas to be 30.321 times higher than the gas utilization rate of the control group, the volumetric utilization rate of the $CO_2$/$CH_4$/$H_2$ mixed gas to be 16.628 times higher than the volumetric utilization rate of the control group, and the dry mycelium weight to be 2.839 times higher than the dry mycelium weight of the control group. It can be known that the *Aspergillus cejpii* S8 strain provided by the present disclosure demonstrates a prominent utilization effect for the $CO_2$/$CH_4$/$H_2$ mixed gas with a strong $CO_2$/$CH_4$/$H_2$ utilization capacity and can utilize the $CO_2$/$CH_4$/$H_2$ mixed gas as a carbon source and an energy source for growth and reproduction.

According to the above examples, the *Aspergillus cejpii* S8 strain of the present disclosure can efficiently metabolize a flammable and explosive gas and a mixed gas including the flammable and explosive gas.

Although the present disclosure has been described in detail through the above examples, the examples are merely some rather than all of the examples of the present disclosure. Other examples can be acquired by a person based on these examples without creative efforts, and these examples shall fall within the protection scope of the present disclosure.

What is claimed:

1. A method for metabolizing a gas, comprising placing *Aspergillus cejpii* S8 or a microbial agent comprising *Aspergillus cejpii* S8 in an atmosphere of the gas, wherein the gas is hydrogen or a mixed gas and the accession number of *Aspergillus cejpii* S8 is CGMCC NO. 40828;
    wherein the mixed gas comprises one or more mixed gases selected from the group consisting of the following:
    (1) hydrogen and carbon dioxide;
    (2) hydrogen and methane; and
    (3) hydrogen, methane, and carbon dioxide.
2. The method according to claim 1, wherein the microbial agent is a suspension of *Aspergillus cejpii* S8.
3. The method according to claim 1, wherein in the mixed gas of (1), a volume ratio of the hydrogen to the carbon dioxide is (1-2):(1-2).
4. The method according to claim 1, wherein in the mixed gas of (2), a volume ratio of the hydrogen to the methane is (1-2):(1-2).
5. The method according to claim 1, wherein in the mixed gas of (3), hydrogen, methane, and carbon dioxide are in a volume ratio of 1:1:1.

* * * * *